United States Patent [19]

Döbert et al.

[11] Patent Number: 6,100,433
[45] Date of Patent: Aug. 8, 2000

[54] PROCESS FOR PREPARING 3-METHOXY-1-PROPANOL

[75] Inventors: Frank Döbert, Köln; Bernd-Michael König, Bergisch Gladbach; Paul Wagner, Düsseldorf; Alexander Klausener, Pulheim, all of Germany

[73] Assignee: Bayer Aktiengesellschaft, Leverkusen, Germany

[21] Appl. No.: 09/285,156

[22] Filed: Apr. 1, 1999

[30] Foreign Application Priority Data

Apr. 7, 1998 [DE] Germany .................. 198 15 634

[51] Int. Cl.[7] .................................................. C07C 43/00
[52] U.S. Cl. .................................................. 568/678
[58] Field of Search ................................ 568/678

[56] References Cited

U.S. PATENT DOCUMENTS 5,112,595  5/1992  Woulfe et al. ........................ 424/1.1

FOREIGN PATENT DOCUMENTS

| 222 059 | 5/1987 | European Pat. Off. . |
| 0 268 956 | 4/1998 | European Pat. Off. . |
| 579651 | 6/1933 | Germany . |
| 8-113564 | 5/1996 | Japan . |

OTHER PUBLICATIONS

J. Org. Chem. 46, p. 531, (month unavailable) 1981.
J. Chem. Soc. Perkin. Trans. I, p. 1807, ( month unavailable) 1981.
J. Chem. Amer. Soc. 76, p. 56, (month unavailable) 1954.
Can. J. Chem. 42, p. 2113, (month unavailable) 1964.
Can J. Chem. 63, p. 1833, (month unavailable) 1985.
Amer. Chem. Soc. 65, p. 1276, (month unavailable) 1943.

*Primary Examiner*—James H. Reamer
*Attorney, Agent, or Firm*—Joseph C. Gil; Diderico van Evl

[57] ABSTRACT

3-Methoxy-1-propanol is prepared in an advantageous manner by alkylating 1,3-propanediol with methyl chloride in the presence of a base.

12 Claims, No Drawings

PROCESS FOR PREPARING 3-METHOXY-1-PROPANOL

FIELD OF THE INVENTION

The present invention relates to a process for preparing 3-methoxy-1-propanol from 1,3-propanediol.

BACKGROUND OF THE INVENTION

3-Methoxy-1-propanol is used as a synthesis building block for preparing pharmaceutically active compounds. It can be employed, for example, in the synthesis of a stomach therapeutic (see EP-A 268,956).

Various methods for preparing 3-methoxy-1-propanol are known. However, all of them have disadvantages. Can. J. Chem. 42, 2113 (1964), for instance, describes the preparation of 3-methoxy-1-propanol from 3-chloro-1-propanol using sodium methoxide in methanol. According to this process, sodium methoxide is initially charged in methanol and 3-chloro-1-propanol is added at boiling point. The yield of 3-methoxy-1-propanol is only 21%. JP Published Specification 08-113546 likewise describes the methoxylation of 3-chloro-1-propanol with sodium methoxide. A yield of 69.8% is said to have been obtained, a result which is still unsatisfactory.

For the reaction of 3-bromo-1-propanol with sodium methoxide, only a yield of 20% is described (see Helv. Chim. Acta 63, 2152 (1980)).

Can. J. Chem. 63, 1833 (1985) describes the formation of 3-methoxy-1-propanol from sodium 3-hydroxypropylate with methyl iodide, J. Amer. Chem. Soc. 65, 1276 (1943). A disadvantage of this process is the fact that expensive methyl iodide is used as a reagent and that a yield of only 64% is obtained.

Furthermore, it is known to prepare 3-methoxy-1-propanol by reaction of 3-methoxypropionaldehyde (see DE 579,651 and Can. J. Chem. 63, 1833 (1985)), by hydration of 3-methoxypropene with mercury acetate and sodium borohydride (see J. Org. Chem. 46, 531 (1981)), by ring-opening of 1,3-dioxane with boron halides (see J. Chem. Soc. Perkin. Trans. I, 1807 (1981)) and by basic or acidic ring opening of oxetane with methanol (see J. Amer. Chem. Soc. 76, 56 (1954)). Disadvantages of these methods are the use of expensive reagents, low yields and the toxic salts which are formed in some cases. These processes are also uneconomical, and some of them require particular ecological expenses.

It is therefore an object of the present invention to provide an economically and ecologically favorable process for preparing 3-methoxy-1-propanol which uses readily available and inexpensive starting materials and provides good yields of desired product.

SUMMARY OF THE INVENTION

This invention, accordingly, provides a process for preparing 3-methoxy-1-propanol which comprises alkylating 1,3-propanediol with methyl chloride in the presence of a base. If appropriate, solvents and/or auxiliaries, such as catalysts, may additionally be employed.

DETAILED DESCRIPTION OF THE INVENTION

The process according to the invention has the advantage that 3-methoxy-1-propanol can be prepared directly and simply from inexpensive and readily available starting materials, without any particular ecological expense. Surprisingly, the process according to the invention proceeds very selectively and gives unexpectedly high yields. Thus, the process is distinguished by the fact that few byproducts are formed and that the starting material 1,3-propanediol is utilized in an excellent manner.

The reaction according to the invention of 1,3-propanediol with methyl chloride in the presence of a base can generally be carried out in all solvents which are stable under the reaction conditions employed. Particularly suitable are polar aprotic solvents, for example ketones such as acetone, diethyl ketone, diisopropyl ketone and methyl ethyl ketone, nitriles such as acetonitrile, amides, such as dimethylformamide, dimethylacetamide and N-methylpyrrolidone, sulfoxides such as dimethyl sulfoxide, sulfones such as sulfolane, hexamethylphosphoric triamide, ethers, such as diethyl ether, diisopropyl ether, tetrahydrofuran, 1,4-dioxane, t-butyl methyl ether, ethylene glycol dimethyl ether and 1,3-dimethoxypropane, and acetals (which are liquid under the reaction conditions) such as formaldehyde dimethyl acetal, 2,2-dimethoxypropane, 1,3-dioxolane and 1,3-dioxane. It is also possible to employ, for example, $C_6$–$C_{10}$-aliphatics such as n-hexane, n-heptane, n-octane, isooctane and n-nonane, and optionally substituted $C_6$- to $C_{10}$-aromatics, such as benzene, toluene, o-, m- and p-cresol, chlorobenzenes, fluorobenzenes and dichlorobenzenes, as solvents. These solvents can in each case be employed on their own or in any mixtures with each other.

In a preferred embodiment, an excess of 1,3-propanediol is used, so that it acts both as reaction partner and as solvent.

Independently of the presence of solvents, the ratio of the amount of 1,3-propanediol which is not consumed during the reaction to the amount of 1,3-propanediol which is consumed in the reaction can be varied over a wide range. The ratio is usually between 50:1 and 0.1:1, preferably between 10:1 and 0.5:1, particularly preferably between 5:1 and 1:1.

Suitable bases are in particular those having a high proton affinity, which are sufficiently stable under the reaction conditions employed and which are suitable for deprotonating alcoholic hydroxyl groups.

Suitable bases are, for example, alkali metal and alkaline earth metal hydroxides, bicarbonates and carbonates, organometallic compounds such as alkyllithium, aryl-lithium and alkylzinc compounds and Grignard reagents, and also organic nitrogen bases having a higher molecular weight, e.g., 1,4-diazabicyclo[2.2.2]octane (DABCO) or 1,8-diazabicyclo[5.4.0]undec-7-ene (DBU). Preference is given to using alkali metal and alkaline earth metal hydroxides; sodium hydroxide and potassium hydroxide are particularly preferred. The base in question can be added to he reaction mixture, for example in solid, dissolved or suspended form. If alkali metal or alkaline earth metal hydroxides are used, it may be of particular advantage to introduce these bases into the reaction mixture as aqueous solutions. Such aqueous alkali metal or alkaline earth metal hydroxide solutions may have a concentration of more than 1% by weight, preferably of more than 10% by weight and particularly preferably a concentration of more than 30% by weight. The ratio of the added base to 1,3-propanediol can be, for example, between 1:0.5 and 1:50, preferably between 1:1 and 1:20, particularly preferably between 1:1 and 1:5.

In principle, the reaction according to the invention of 1,3-propanediol with methyl chloride in the presence of a base can be carried out batchwise or continuously.

In a preferred batchwise embodiment, the process according to the invention is carried out in a semi-batch process where gaseous methyl chloride and base in liquid form are metered in simultaneously to 1,3-propanediol which is, if appropriate, mixed with further solvent.

In a preferred continuous embodiment, methyl chloride and base are metered in continuously to a stream of 1,3-propanediol.

Independently of the way in which the process according to the invention is carried out, methyl chloride and base can be added simultaneously or successively, at one common location or spatially separated from one another. If the addition is carried out at different locations or at different times, it is advantageous to meter in first the base and then the methyl chloride.

If the process according to the invention is carried out batchwise, for example in a semi-batch process, a suitable reaction apparatus for this purpose is generally a customary stirred-tank reactor which is operated batchwise. Such a stirred-tank reactor is preferably fitted with stirring elements which ensure a good introduction of the gaseous methyl chloride into the reaction medium, such as gassing stirrers, toothed-disk stirrers, multistage-impulse countercurrent agitators or other gassing stirrers known to the person skilled in the art. The addition of methyl chloride is then carried out using such stirrer elements fitted with devices for gassing.

If the process according to the invention is carried out continuously, suitable reaction apparatus for this purpose are, for example, customary continuously-operated stirred-tank reactors, stirred-tank cascades or various types of tubular reactors, e.g., bubble column reactors, tubular-flow reactors, loop reactors or other systems known to the person skilled in the art which are suitable for carrying out continuous reactions.

In a particularly preferred variant of the process according to the invention, 1,3-propanediol is initially reacted with an alkali metal or alkaline earth metal hydroxide which is, if appropriate, dissolved in water, and the resulting water of reaction and, if appropriate, water which was introduced into the reaction mixture is removed from the reaction mixture prior to the addition of methyl chloride. This dewatering is possible, for example, by a simple distillation, which can be carried out at atmospheric pressure or at reduced pressure. In a more gentle manner, the water can be removed by an azeotropic distillation. Suitable azeotrope formers are substances which are capable of forming a heteroazeotrope with water, such as 2-methoxyethanol, dimethoxymethane, trimethylamine, 1-butyn-3-one, 3-butene-nitrile, methacrylonitrile, dioxene, butyronitrile, 2-butanone, ethyl vinyl ether, tetrahydrofuran, dioxane, ethyl acetate, methyl propionate, propyl formate, diethyl ether, methyl propyl ether, 1,1-dimethoxyethane, 1,2-dimethoxyethane, 2-ethoxyethanol, isopropyl formate, ethoxymethoxymethane, 1-methoxy-2-propanol, 2-methoxy-1-propanol, 3-methoxy-1-propanol, furfural, 2-methylfuran, allyl vinyl ether, cyclopentanone, 1-methoxy-1,3-butadiene, 1,3-dimethoxypropane, 2-methyl-3-butyn-2-ol, allyl acetate, 2,3-pentanedione, 2,4-pentanedione, vinyl propionate, cyclopentanol, isopropenyl ethyl ether, isopropyl vinyl ether, 2-pentanone, 3-pentanone, propyl vinyl ether, butyl formate, propyl acetate, 2-methoxy-ethyl acetate, methoxymethyl propionate, n-amyl alcohol, tert-amyl alcohol, tert-isobutyl methyl ether, ethyl propyl ether, isoamyl alcohol, 3-methylbutanol, 2-pentanol, 3-pentanol, 1,2-dimethoxypropane, 1-ethoxy-2-propanol, 1,1,2-trimethoxyethane, cyclohexene, 2-ethyl-1,3-butadiene, 1-hexen-5-one, cyclohexane, 1-hexene, 4-methyl-2-pentene, cyclohexanol, 2-hexanone, 3-hexanone, 4-methyl-2-pentanone, amyl formate, butyl acetate, hexane, tert-amyl methyl ether, butyl ethyl ether, diisopropyl ether, aromatic hydrocarbons and other substances known to the person skilled in the art which are capable of forming an azeotrope with water. In a preferred variant of the azeotropic distillation, toluene or benzene is employed for entraining out of the water.

The removal of water can be carried out batchwise or continuously.

In this preferred variant of the process according to the invention, the dehydrated reaction solution is then reacted with methyl chloride.

To accelerate the methylation reaction according to the invention, it is possible to add, if appropriate, bromine salts or iodine salts as catalysts to the reaction mixture. Particularly suitable for this purpose are alkali metal and alkaline earth metal bromides and iodides. Preference is given to adding catalytic amounts of sodium iodide or potassium iodide to the reaction mixture. Such salts may be employed, for example, in amounts of from 0.001 to 10% by weight, preferably from 0.01 to 5% by weight, particularly preferably from 0.1 to 2% by weight, based in each case on the total reaction mixture.

To obtain high space-time yields, it is advantageous to carry out the process according to the invention in a temperature range between 50 and 200° C., preferably between 70 and 160° C. and particularly preferably between 80 and 150° C.

The methyl chloride may be added to the reaction mixture in gaseous form or in liquefied form, and liquefaction may be carried out by pressure and/or cooling. Preference is given to adding gaseous methyl chloride to the reaction mixture. Here, the partial pressure of the methyl chloride may be, for example, between 0.01 and 10 bar, preferably between 0.1 and 5 bar, particularly preferably between 0.5 and 4 bar. The methyl chloride pressure can be varied as the reaction progresses. Thus, it may be advantageous to increase the pressure toward the end of the reaction.

The reaction according to the invention can be carried out, for example, with residence times between 1 sec and 10 h, preferably between 1 min and 5 h, particularly preferably between 10 min and 4 h.

The actual pressure in the reaction apparatus depends on the rate of reaction. Usually, the total pressure during the reaction is from 0.01 to 50 bar, preferably from 0.1 to 10 bar, particularly preferably from 0.5 to 5 bar.

The molar ratio of methyl chloride to base may be, for example, between 0.1 and 10, preferably between 0.5 and 5 and particularly preferably between 0.8 and 1.2.

Work-up of the reaction mixture can be carried out in a manner known in principle. For example, the salt formed from the base during the reaction can be initially separated off, for example by filtration. Such a filtration can be carried out in a customary apparatus which is suitable for separating off solids, e.g., nutsch filters, belt filters, leaf filters, cartridge filters, filter presses, rotary filters, pressure drum filters and rotary pressure filters. The salt can also be removed by centrifugation. The filtrate essentially contains unreacted 1,3-propanediol and 1,3-propanediol which was optionally employed as solvent, further solvent which is optionally present, excess base which is optionally present, the 3-methoxy-1-propanol which has been prepared, and also generally a very small proportion of 1,3-dimethoxypropane. This mixture can be separated into the individual components in a manner known to the person skilled in the art, preferably by distillation. 1,3-Propanediol which has been separated off can be recycled for further reaction.

A particular advantage of the process according to the invention is the high selectivity of the reaction of the starting materials. The selectivity of the formation of 3-methoxy-1-propanol which can be obtained is generally greater than 85%, frequently greater than 90% and may even be greater than 95%.

The examples which follow are intended to illustrate the process according to the invention without imposing any limitations.

EXAMPLES

Example 1

315 g of 1,3-propanediol were initially charged in a 1 l multi-necked flask. 224g of a 50% strength by weight aqueous potassium hydroxide solution were metered in. The resulting mixture was distilled under reduced pressure until free of water. In this manner, 388 g of a solution of the monopotassium alkoxide of 1,3-propanediol were obtained.

Under nitrogen, 311 g of the solution thus prepared were initially charged, together with 3 g of potassium iodide, in an autoclave. The mixture was heated to 120° C. and admixed with methyl chloride which was introduced into the reactor under a pressure of 2 bar over a period of 1.7 hours. The solution was subsequently stirred at 120° C. for another hour. A total of 84 g of methyl chloride was taken up.

According to gas chromatographic analysis, the reaction product contained, after cooling and removal of the precipitated potassium chloride by filtration, 55% of 1,3-propanediol, 38% of 3-methoxy-1-propanol and 5% of dimethoxypropane. Thus, the selectivity of the formation of 3-methoxy-1-propanol was 89% and its yield was 71% of theory, in each case based on the monopotassium salt of 1,3-propanediol employed.

Example 2 a) 4560 g of 1,3-propanediol were initially charged, together with 495.3 g of powdered potassium hydroxide (85% pure by weight), in a 6 l multi-necked flask. 832 g of a 50% strength by weight aqueous potassium hydroxide solution were metered in. The resulting mixture and 200 ml of toluene were distilled azeotropically until free of water. In this manner, 5189 g of a solution of the monopotassium salt of 1,3-propanediol were obtained.

b) Under nitrogen, 2060 g of the solution thus prepared were initially charged, together with 20 g of potassium iodide, in an autoclave. The mixture was heated to 100° C. and admixed with methyl chloride which was introduced into the reactor under a pressure of 2 bar for a period of 2 hours. A total of 302 g of methyl chloride were taken up. According to gas chromatographic analysis, the reaction product contained, after cooling and removal of the precipitated potassium chloride via filtration, 73% of 1,3-propanediol, 21% of 3-methoxypropanol and 1% of dimethoxypropane. Thus, the selectivity of formation of 3-methoxy-1-propanol was 96% and its yield was 85% of the theory, in each case based on the monopotassium salt of 1,3-propanediol employed.

Example 3

Under nitrogen, 256 g of a solution of the monopotassium salt of 1,3-propanediol obtained according to Example 2 a) were initially charged in an autoclave. The mixture was heated to 100° C. and admixed with methyl chloride which was initially introduced into the reactor under a pressure of 2 bar over a period of 1.3 hours and subsequently under a pressure of 3 bar over a period of 1.3 hours.

A total of 38 g of methyl chloride were taken up. According to gas chromatographic analysis, the reaction product contained, after cooling and removal of the precipitated potassium chloride by filtration, 74% of 1,3-propanediol, 23% of 3-methoxy-1-propanol and 2% of dimethoxy-propane. Thus, selectivity of the formation of 3-methoxy-1-propanol was 93% and its yield was 82% of the theory, in each case based on the monopotassium salt of 1,3-propanediol employed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 3-methoxy-1-propanol comprising alkylating 1,3-propanediol with methyl chloride in the presence of a base component.

2. The process of claim 1, wherein the reaction is carried out in the presence of a solvent component comprising a component selected from the group consisting of ketones, nitriles, amides, sulfoxides, sulfones, hexamethylphosphoric triamide, ethers, acetals which are liquid under the reaction conditions, $C_6$–$C_{10}$-aliphatics and optionally substituted $C_6$–$C_{10}$-aromatics.

3. The process of claim 1, wherein an excess of 1,3-propanediol is used.

4. The process of claim 1, wherein the base component employed is sufficiently stable under the reaction conditions and is suitable for deprotonating alcoholic hydroxide groups.

5. The process of claim 1, wherein the molar ratio of the added base to 1,3-propanediol is between 1:0.5 and 1:50.

6. The process of claim 1, wherein the process carried out batchwise.

7. The process of claim 1, wherein the process is carried out continuously.

8. The process of claim 1, wherein 1,3-propanediol is initially reacted with alkali metal or alkaline earth metal hydroxide and water resulting from the reaction.

9. The process of claim 1, wherein water is introduced into the reaction mixture and is removed from the reaction mixture prior to the addition of methyl chloride.

10. The process of claim 1, wherein bromine or iodine salts are added to the reaction mixture as catalysts.

11. The process of claim 1, wherein the process is carried out at temperatures in the range from 50 to 200° C., methyl chloride partial pressures in the range from 0.01 to 10 bar and total pressures in the range from 0.01 to 50 bar.

12. The process of claim 1, wherein the solvent used is 1,3-propanediol.

* * * * *